(12) United States Patent
McShane et al.

(10) Patent No.: US 8,747,479 B2
(45) Date of Patent: Jun. 10, 2014

(54) TIBIAL COMPONENT

(76) Inventors: Michael A. McShane, Columbus, OH (US); Donald J. Hackman, Columbus, OH (US)

( * ) Notice: Subject to any disclaimer, the term of this patent is extended or adjusted under 35 U.S.C. 154(b) by 0 days.

(21) Appl. No.: 13/457,190

(22) Filed: Apr. 26, 2012

(65) Prior Publication Data

US 2012/0277881 A1    Nov. 1, 2012

Related U.S. Application Data

(60) Provisional application No. 61/517,808, filed on Apr. 26, 2011, provisional application No. 61/638,062, filed on Apr. 25, 2012.

(51) Int. Cl.
*A61F 2/38* (2006.01)

(52) U.S. Cl.
USPC .................................. 623/20.32; 623/20.31

(58) Field of Classification Search
USPC ........... 623/14.12, 20.28, 20.29, 20.32–20.34
See application file for complete search history.

(56) References Cited

U.S. PATENT DOCUMENTS

| | | |
|---|---|---|
| 3,916,451 A | 11/1975 | Buechel et al. |
| 4,085,466 A | 4/1978 | Goodfellow et al. |
| 4,213,209 A | 7/1980 | Insall et al. |
| 4,224,696 A | 9/1980 | Murray et al. |
| 4,224,697 A | 9/1980 | Murray et al. |
| 4,298,992 A | 11/1981 | Burstein et al. |
| 4,309,778 A | 1/1982 | Buechel et al. |
| 4,314,381 A | 2/1982 | Koeneman |
| 4,340,978 A | 7/1982 | Buechel et al. |
| 4,365,359 A | 12/1982 | Raab |
| 4,586,933 A | 5/1986 | Shoji et al. |
| 4,642,124 A | 2/1987 | Cooke |
| 4,892,551 A | 1/1990 | Haber |
| 4,911,718 A | 3/1990 | Lee et al. |
| 4,959,071 A | 9/1990 | Brown et al. |
| 5,080,675 A | 1/1992 | Lawes et al. |
| 5,123,927 A | 6/1992 | Duncan et al. |
| 5,201,881 A | 4/1993 | Evans |
| 5,226,915 A | 7/1993 | Bertin |
| 5,330,534 A | 7/1994 | Herrington et al. |
| 5,358,529 A | 10/1994 | Davidson |
| 5,370,699 A | 12/1994 | Hood et al. |
| 5,387,240 A | 2/1995 | Pottenger et al. |
| 5,389,107 A | 2/1995 | Nassar et al. |
| D358,211 S | 5/1995 | Cohen |
| 5,413,604 A | 5/1995 | Hodge |
| 5,456,717 A | 10/1995 | Zweymuller et al. |
| 5,458,643 A | 10/1995 | Oka et al. |
| 5,507,820 A | 4/1996 | Pappas |
| 5,509,934 A | 4/1996 | Cohen |

(Continued)

OTHER PUBLICATIONS

Steven M. Kurtz, "The UHMWPE Handbook, Ultra-High Molecular Weight Polyethylene in Total Joint Replacement," pp. 158-159, 2004, Elsevier Press, San Diego, CA.

(Continued)

*Primary Examiner* — Thomas J Sweet
*Assistant Examiner* — Megan Wolf
(74) *Attorney, Agent, or Firm* — Thomas Y. Kendrick; Benesch Friedlander Coplan & Aronoff LLP (57) ABSTRACT

Methods, systems, and apparatuses are disclosed for a tibial component having shock absorbing features.

15 Claims, 8 Drawing Sheets

(56) References Cited

U.S. PATENT DOCUMENTS

| | | |
|---|---|---|
| 5,545,229 A | 8/1996 | Parsons et al. |
| 5,549,686 A | 8/1996 | Johnson et al. |
| 5,609,639 A | 3/1997 | Walker |
| 5,609,643 A | 3/1997 | Colleran et al. |
| 5,702,458 A | 12/1997 | Burstein et al. |
| 5,733,292 A | 3/1998 | Gustilo et al. |
| 5,776,200 A | 7/1998 | Johnson et al. |
| 5,782,925 A | 7/1998 | Collazo et al. |
| 5,824,103 A * | 10/1998 | Williams .................. 623/20.32 |
| 5,928,286 A | 7/1999 | Ashby et al. |
| 5,957,979 A | 9/1999 | Beckman et al. |
| 6,197,065 B1 | 3/2001 | Martin et al. |
| 6,242,507 B1 | 6/2001 | Saum et al. |
| 6,258,126 B1 | 7/2001 | Colleran |
| 6,264,697 B1 | 7/2001 | Walker |
| 6,315,798 B1 | 11/2001 | Ashby et al. |
| 6,319,283 B1 | 11/2001 | Insall et al. |
| 6,336,941 B1 | 1/2002 | Subba Rao et al. |
| 6,361,564 B1 | 3/2002 | Marceaux et al. |
| 6,365,089 B1 | 4/2002 | Krebs et al. |
| 6,402,786 B1 | 6/2002 | Insall et al. |
| 6,406,497 B2 | 6/2002 | Takei |
| 6,508,841 B2 | 1/2003 | Martin et al. |
| 6,645,251 B2 | 11/2003 | Salehi et al. |
| 6,652,587 B2 | 11/2003 | Felt et al. |
| 6,709,438 B2 | 3/2004 | Dixon et al. |
| 6,712,855 B2 | 3/2004 | Martin et al. |
| 6,770,099 B2 | 8/2004 | Andriacchi et al. |
| 6,835,207 B2 | 12/2004 | Zacouto et al. |
| 6,855,165 B2 | 2/2005 | Fell et al. |
| 6,875,235 B2 | 4/2005 | Ferree |
| 6,887,278 B2 | 5/2005 | Lewallen |
| 6,972,039 B2 | 12/2005 | Metzger et al. |
| 7,066,958 B2 | 6/2006 | Ferree |
| 7,070,622 B1 | 7/2006 | Brown et al. |
| 7,083,652 B2 | 8/2006 | McCue et al. |
| 7,094,259 B2 | 8/2006 | Tarabichi |
| 7,105,027 B2 | 9/2006 | Lipman et al. |
| 7,108,720 B2 | 9/2006 | Hanes |
| 7,186,364 B2 | 3/2007 | King et al. |
| 7,198,642 B2 | 4/2007 | Hazebrouck et al. |
| 7,205,051 B2 | 4/2007 | King et al. |
| 7,211,113 B2 | 5/2007 | Zelener et al. |
| 7,214,764 B2 | 5/2007 | King |
| 7,235,102 B2 | 6/2007 | Ferree et al. |
| 7,244,274 B2 | 7/2007 | Delfosse et al. |
| 7,255,715 B2 | 8/2007 | Metzger |
| 7,288,115 B2 | 10/2007 | Hawkins |
| 7,374,575 B2 | 5/2008 | Curradini |
| 7,429,346 B2 | 9/2008 | Ensign et al. |
| 7,465,320 B1 | 12/2008 | Kito et al. |
| 7,470,288 B2 | 12/2008 | Dietz et al. |
| 7,491,235 B2 | 2/2009 | Fell |
| 7,497,874 B1 | 3/2009 | Metzger et al. |
| 7,527,650 B2 | 5/2009 | Johnson et al. |
| 7,582,118 B2 | 9/2009 | Brown et al. |
| 7,635,390 B1 | 12/2009 | Bonutti |
| 7,658,767 B2 | 2/2010 | Wyss |
| 7,695,520 B2 | 4/2010 | Metzger et al. |
| 7,722,678 B2 | 5/2010 | Brown et al. |
| 7,749,229 B1 | 7/2010 | Bonutti |
| 7,776,097 B2 | 8/2010 | Tepic et al. |
| 7,790,095 B2 | 9/2010 | Muratoglu et al. |
| 7,794,504 B2 | 9/2010 | Case |
| 7,803,193 B2 | 9/2010 | Steinberg |
| 7,806,896 B1 | 10/2010 | Bonutti |
| 7,806,935 B2 | 10/2010 | Navarro et al. |
| 7,837,736 B2 | 11/2010 | Bonutti |
| 7,837,738 B2 | 11/2010 | Reigstad et al. |
| 7,842,092 B2 | 11/2010 | Otto et al. |
| 7,842,093 B2 | 11/2010 | Peters et al. |
| 7,863,348 B2 | 1/2011 | Abt et al. |
| 7,871,442 B2 | 1/2011 | Servidio |
| 7,892,288 B2 | 2/2011 | Blaylock et al. |
| 8,092,533 B2 | 1/2012 | Melkent |
| 2004/0006394 A1 | 1/2004 | Lipman et al. |
| 2004/0266903 A1 | 12/2004 | King |
| 2005/0149199 A1 * | 7/2005 | Steinberg ................... 623/22.23 |
| 2006/0064169 A1 | 3/2006 | Ferree |
| 2008/0033567 A1 | 2/2008 | Stchur |
| 2008/0086210 A1 * | 4/2008 | Fox ............................ 623/14.12 |
| 2008/0243127 A1 | 10/2008 | Lang et al. |
| 2008/0275565 A1 | 11/2008 | Makower et al. |
| 2009/0036993 A1 | 2/2009 | Metzger |
| 2009/0143869 A1 | 6/2009 | Cheng et al. |
| 2010/0121457 A1 | 5/2010 | Clifford et al. |
| 2010/0191342 A1 | 7/2010 | Byrd et al. |
| 2011/0015750 A1 | 1/2011 | Popoola et al. |
| 2011/0046741 A1 | 2/2011 | Khandkar et al. |
| 2011/0125275 A1 | 5/2011 | Lipman et al. |

OTHER PUBLICATIONS

T. D. Brown & D. L. Bartel, "What Design Factors Influence Wear Behavior at the Bearing Surfaces in Total Joint Replacements?", J Am Acad Orthop Surg, Jul. 2008, vol. 16 No. suppl. 1 S101-S106.

Moximed, "KineSpring Knee Implant System: The First of Its Kind." www.moximed.com/ous/medpros, 2012.

* cited by examiner

TIBIAL COMPONENT

CROSS-REFERENCE TO RELATED APPLICATIONS

This application claims priority from U.S. Provisional Patent Application No. 61/517,808, filed on Apr. 26, 2011, and U.S. Provisional Patent Application No. 61/638,062, filed on Apr. 25, 2012, each of which is incorporated by reference herein in its entirety.

BACKGROUND

A common health concern today is the wearing out of one's joints due to such factors as age, over-exertion, health, injury, and weight. In many instances, joints are replaced in a medical procedure to relieve the pain and loss of function often associated with joint wearing. Total knee replacement ("TKR") is one such procedure. TKR involves the removal of a patient's entire knee joint, followed by the implant of prosthetic knee components. Approximately 581,000 TKR procedures are performed annually in the United States.

Knee prostheses typically last between about 15 and 20 years in a patient, by which point the prostheses has typically worn to a point of needing replacement. However, this wearing of knee prostheses can cause long-term complications well before the complete wearing of the prostheses, requiring surgery and replacement of the prosthesis prematurely. One such long-term complication is osteolysis, wherein particulate debris from wear of prosthetic components causes a local immune response, resulting in tissue damage and bone resorption. Osteolysis, which occurs in up to 10% of knee replacement patients, can cause a knee prosthesis to loosen, and in some instances can cause the bone to fracture in areas immediately surrounding the implant.

Studies have shown that excessive wear of knee prostheses and generation of particulates are often the product of high contact stress and shear forces exerted by rigid metal knee prosthesis components upon polymer knee components. Reduction of these high contact stress and shear forces is shown to increase the life of knee prostheses and decrease the generation of particulate debris from the TKR. Also, to generate a cushioning within a prosthesis can reduce peak loads and further reduce contact stress and shear forces. This results in a prosthesis that behaves and feels more like a natural knee, which in turn provides for greater patient mobility and comfort. What is needed is an improved tibial component configured to better manage the loads within a TKR through cushioning and shock absorbing features integrated into the tibial component.

SUMMARY

In one embodiment, a tibial component of a knee joint prosthesis is provided, the tibial component comprising: a body portion; an upper surface; a first concave fossae comprising a first condyle contact surface; a second concave fossae comprising a second condyle contact surface; a lower surface; a side portion extending between the upper surface and the lower surface; a first bearing portion; a second bearing portion; and at least one cavity extending into the body portion from the lower surface; wherein a load applied substantially normally to the first condyle contact surface and the second condyle contact surface causes a tensile stress within the first bearing portion and the second bearing portion, and a compressive stress within the side portion.

In another embodiment, a tibial component of a knee joint prosthesis is provided, the tibial component comprising: a body portion; an upper surface; a first concave fossae comprising a first condyle contact surface; a second concave fossae comprising a second condyle contact surface; a lower surface; a side portion extending between the upper surface and the lower surface; a first bearing portion; a second bearing portion; and at least one cavity extending into the body portion from the side portion; wherein a load applied substantially normally to the first condyle contact surface and the second condyle contact surface causes a tensile stress within the first bearing portion and the second bearing portion, and a compressive stress within the side portion.

In another embodiment, a total knee joint prosthesis, the total knee joint prosthesis comprising: a substantially rigid femoral component comprising a first condyle and a second condyle; and a substantially rigid tibial component, comprising: a body portion; an upper surface; a first concave fossae comprising a first condyle contact surface; and a second concave fossae comprising a second condyle contact surface; a lower surface; a side portion extending between the upper surface and the lower surface; a first bearing portion; a second bearing portion; and at least one cavity; wherein the first condyle operatively connects to the first condyle contact surface and the second condyle operatively connects to the second condyle contact surface; and wherein a load applied by the first condyle and the second condyle substantially normally to the first condyle contact surface and the second condyle contact surface causes a tensile stress within the first bearing portion and the second bearing portion, and a compressive stress within the side portion.

BRIEF DESCRIPTION OF THE DRAWINGS

The accompanying figures, which are incorporated in and constitute a part of the specification, illustrate various example apparatuses, systems, and methods, and are used merely to illustrate various example embodiments.

DETAILED DESCRIPTION

Figure 1:
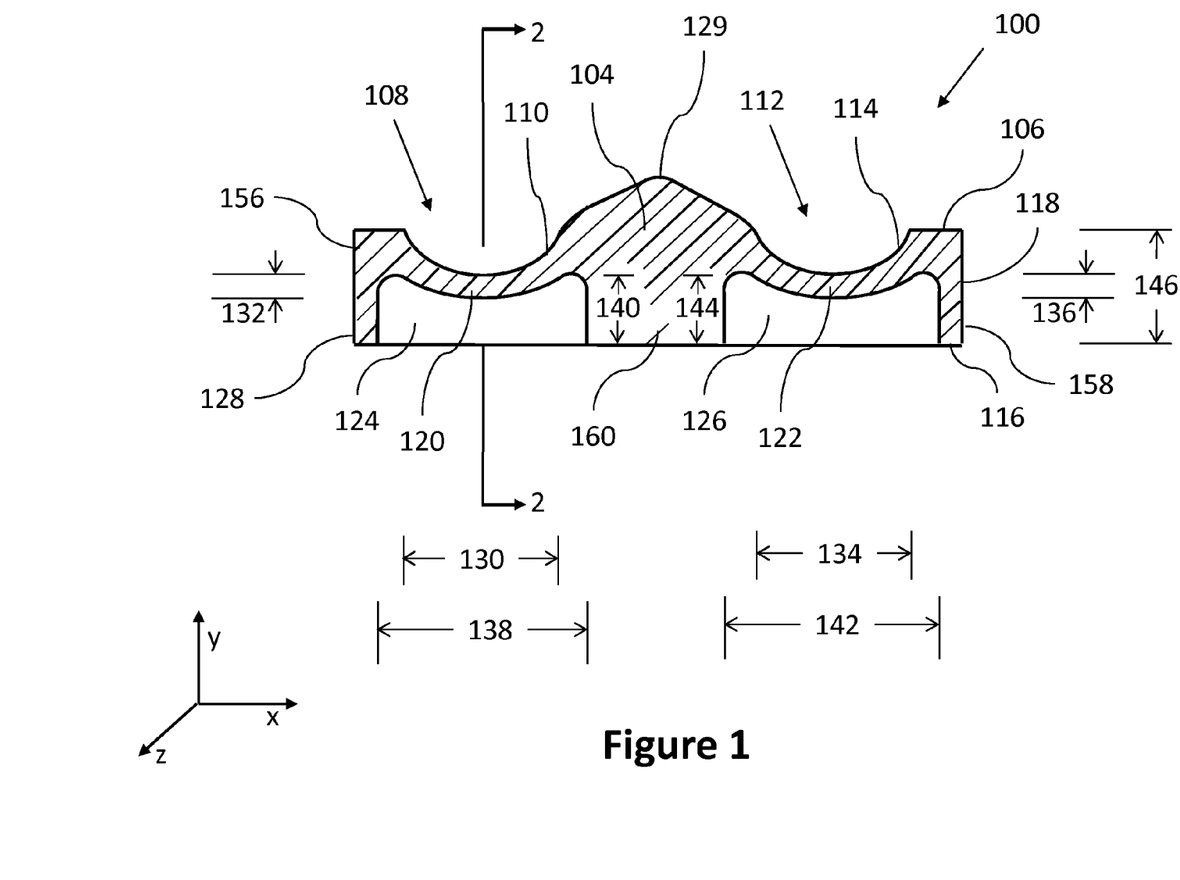
FIG. 1 illustrates an example arrangement of a tibial component of a knee joint prosthesis.

FIG. 1 illustrates a front view of an example arrangement of a tibial component 100 of a total knee joint prosthesis, including a body portion 104 and an upper surface 106. Tibial component 100 further comprises a first concave fossae 108 including a first condyle contact surface 110, as well as a second concave fossae 112 including a second condyle contact surface 114. Tibial component 100 additionally includes a lower surface 116 and a side portion 118 extending between upper surface 106 and lower surface 116. Tibial component 100 comprises a first bearing portion 120 and a second bearing portion 122. Tibial component 100 includes at least one cavity extending into body portion 104 from lower surface 116, such as first cavity 124 and second cavity 126. Tibial component 100 may additionally include a rim portion 128 capable of operatively connecting tibial component 100 to a substantially rigid tibial tray (not shown). Tibial component 100 may further include a center post 129 extending from body portion 104. Tibial component 100 additionally may also include a first lateral side portion 156, a second lateral side portion 158, and a posterior side portion 160.

Tibial component 100, including body portion 104, may be formed of any of a number of materials, including for example, a polymer, a metal, an alloy, and a composite. In one embodiment, tibial component 100 is comprised of a polymeric material having a Shore hardness equal to or greater than about 90. In one embodiment, tibial component 100 is comprised of a polymeric material having a Shore hardness of about 95. In another embodiment, tibial component 100 may be comprised of a polymeric material having a Shore hardness of greater than 65. In one embodiment, tibial component 100 may be comprised of a polymeric material having a Shore hardness that must be greater than 70. In another embodiment, tibial component 100 may be comprised of a polymeric material having a Shore hardness that must be greater than about 70. In another embodiment, tibial component 100 may be comprised of a polymeric material having a Shore hardness equal to or greater than about 80. In another embodiment, tibial component 100 may be comprised of a polymeric material having a Shore hardness equal to or greater than about 85. In another embodiment, tibial component 100 may be comprised of a polymeric material having a Shore hardness between about 70 and about 95. In another embodiment, tibial component 100 may be comprised of a polymeric material having a Shore hardness between about 75 and about 95. In one embodiment, tibial component 100 may be comprised of a polymeric material having a Shore hardness between 70 and 80. In one embodiment, tibial component 100 may be comprised of a polymeric material having a Shore hardness between about 70 and about 80. In one embodiment, tibial component 100 may be comprised of a polymeric material having a Shore hardness between 80 and 90. In one embodiment, tibial component 100 may be comprised of a polymeric material having a Shore hardness between about 80 and about 90. In one embodiment, tibial component 100 may be comprised of a polymeric material having a Shore hardness between 85 and 95. In one embodiment, tibial component 100 may be comprised of a polymeric material having a Shore hardness between about 85 and about 95. In one embodiment, tibial component 100 may be comprised of a polymeric material having a Shore hardness between 90 and 100. In one embodiment, tibial component 100 may be comprised of a polymeric material having a Shore hardness between about 90 and 100. In one embodiment, tibial component 100 is comprised of a substantially rigid material. In one embodiment, tibial component 100 is comprised of a polymer such as polyethylene. In another embodiment, tibial component 100 is comprised of an Ultra-High Molecular Weight Polyethylene with the following properties: a tensile yield strength of 3,100 lbf/in$^2$ to 4,000 lbf/in$^2$; a compression yield strength at 2% deflection of 2000 lbf/in$^2$ to 2,500 lbf/in$^2$.

First concave fossae 108 and second concave fossae 112 may be configured to engage one or more condyles of a corresponding femoral component (not shown). First concave fossae 108 and second concave fossae 112 may include an xz plane cross-section having any of various shapes, including oval, elliptical, and quadrilateral. First concave fossae 108 and second concave fossae 112 may include an xy plane cross-section having any of various shapes, including semi-circular, semi-elliptical, and quadrilateral. First concave fossae 108 and second concave fossae 112 may include a yz plane cross-section having any of various shapes, including semi-circular and semi-elliptical.

First condyle contact surface 110 and second condyle contact surface 114 may be configured to operatively connect with one or more condyles of a corresponding femoral component (not shown).

First bearing portion 120 and a second bearing portion 122 may be defined between first condyle contact surface 110 and second condyle contact surface 114, and first cavity 124 and second cavity 126, respectively. In one embodiment, first bearing portion 120 and second bearing portion 122 are configured to support at least one condyle of a corresponding femoral component (not shown). In one embodiment, a load applied substantially normally to first condyle contact surface 110 causes a tensile stress within first bearing portion 120. In another embodiment, a load applied substantially normally to second condyle contact surface 114 causes a tensile stress within second bearing portion 122. In another embodiment, a load applied substantially normally to first condyle contact surface 110 and/or second condyle contact surface 114 causes a compressive stress within side portion 118. In one embodiment, a load applied substantially normally to first condyle contact surface 110 causes a compressive stress within first condyle contact surface 110 to a shallow depth. In one embodiment, a load applied substantially normally to second condyle contact surface 114 causes a compressive stress within second condyle contact surface 114 to a shallow depth.

The tensile stress produced in first bearing portion 120 and second bearing portion 122 may cause first bearing portion 120 and second bearing portion 122 to stretch, thereby creating a cushioning effect to the entire knee joint prosthesis. The tensile stress produced in first bearing portion 120 with a first lateral side portion 156 and second bearing portion 122 may cause first bearing portion 120 with second lateral side portion 158 and second bearing portion 122 to deflect slightly while maintaining a state of tension, thereby increasing the contact area between first condyle contact surface 110 and second condyle contact surface 114 and the condyles of a femoral component (not shown), thus significantly decreasing pressure in the contact area and exceptionally prolonging the life of tibial component 100. The junction of first bearing portion 120 and second bearing portion 122 with side portion 118 may experience a shear stress as a result of the vertical component (along the y-axis) of the shallow compressive stress within first condyle contact surface 110 and second condyle contact surface 114. This shear stress at the junction of first bearing portion 120 and second bearing portion 122 with side portion 118 may cause compressive stress within side portion 118. In one embodiment, the compressive stress within side portion 118 allows additional cushioning effect within the entire knee prosthesis.

Tibial component 100 may be comprised of a polymeric material having a Shore hardness of about 90. The rigid nature of the tibial component 100 material having a Shore hardness of about 90 may allow tibial component 100 to redistribute a force applied substantially normally to first condyle contact surface 110 and second condyle contact surface 114, and thus redistribute pressure, from first bearing portion 120 and second bearing portion 122, to side portion 118, as more fully described above. In one embodiment, tibial component 100 is comprised of a polymeric material having a Shore hardness of about 90, which results in first bearing portion 120 and second bearing portion 122 experiencing only slight compression stress at first condyle contact surface 110 and second condyle contact surface 114 as a result of a force applied substantially normally to first condyle contact surface 110 and second condyle contact surface 114, and which results in first bearing portion 120 and second bearing portion 122 experiencing almost exclusively tensile stress about the entirety of first bearing portion 120 and second bearing portion 122. Tibial component 100 having a Shore hardness of about 90 may experience significantly more tensile stress in first bearing portion 120 and second bearing portion 122, thereby resulting in surprisingly effective cushioning in tibial component 100.

In one embodiment, first bearing portion 120 and second bearing portion 122 have a tensile yield stress of between about 3,100 lbf/in$^2$ and about 4,000 lbf/in$^2$. In another embodiment, first bearing portion 120 and second bearing portion 122 have a tensile yield stress less than about 3,100 lbf/in$^2$ or greater than about 4,000 lbf/in$^2$, as may be required to adequately support the weight of specific patients and withstand various levels of patient activity. In one embodiment, first bearing portion 120 and second bearing portion 122 have a compressive yield stress (at about 2% deflection) between about 2,000 lbf/in$^2$ and about 2,500 lbf/in$^2$. In another embodiment, first bearing portion 120 and second bearing portion 122 have a compressive yield stress less than about 2,000 lbf/in$^2$ or greater than about 2,500 lbf/in$^2$, as may be required to adequately support the weight of specific patients and withstand various levels of patient activity.

In practice, tibial component 100 is at least operatively connected to an individual's resected tibia, while a femoral component (not shown) is at least operatively connected to the individual's resected femur. While the individual is standing, the weight of the individual is transferred through the femur to the femoral component (not shown), and from the femoral component into tibial component 100. The femoral component (not shown) may comprise a plurality of condyles (not shown), and at least one for each concave fossae (108, 112) in tibial component 100. The at least one condyle (not shown) may operatively connect to at least one of first condyle contact surface 110, second condyle contact surface 114, upper surface 106, and center post 129. In one embodiment, center post 129 extends adjacent to the at least one condyle (not shown), or between two condyles (not shown), and is configured to limit lateral displacement of the at least one condyle (not shown) relative to tibial component 100.

In one embodiment, tibial component 100 is connected to a tibial tray (not shown), which is in turn connected to an individual's tibia. In one embodiment, tibial component 100 is capable of being connected to a tibial tray (not shown) via rim portion 128. Rim portion 128 may comprise a recessed groove or prominent ridge configured to engage a corresponding ridge or groove within a tibial tray (not shown). In another embodiment, tibial component 100 is capable of being connected directly to an individual's tibia without the use of a tibial tray (not shown).

In one embodiment, the femoral component (not shown) may comprise a first and second condyle (not shown), which are operatively connected to first condyle contact surface 110 and second condyle contact surface 114, respectively. During the natural movements of the human body and the knee joint, one of the first and second condyle (not shown) may experience more or less force than the other. For example, most or all of the weight of the individual may be transferred through the first condyle to first condyle contact surface 110, while little or no weight of the individual is transferred through the second condyle to second condyle contact surface 114. Likewise, during the natural movements of the human body and the knee joint, forces may be transmitted through the condyles (not shown) to tibial component 100 in directions substantially along the y-axis, substantially along the x-axis, substantially along the z-axis, or along a combination of two or more of the y-axis, x-axis, and z-axis.

Natural movements of the human body cause movement of the total knee joint prosthesis about at least two axes of rotation. One such movement of the total knee joint results from flexion and extension, wherein the tibia and tibial component 100 rotates with the femur and femoral component (not shown) about an axis substantially aligned with the x-axis illustrated in FIG. 1. Another movement of the knee joint results from internal and external rotation, wherein the tibia and tibial component 100 rotate relative to the femur and femoral component (not shown) about an axis substantially aligned with the y-axis illustrated in FIG. 1. During these various movements of the human body and knee joint prosthesis, various forces can be transmitted through the one or more condyle (not shown) to tibial component 100. However, the total knee joint prosthesis is configured to in most cases direct such forces from the one or more condyle (not shown) to tibial component 100 substantially normally to one or both of first condyle contact surface 110 and second condyle contact surface 114.

In one embodiment, tibial component 100 includes a plurality of cavities, for example, first cavity 124 and second cavity 126 illustrated in FIG. 1. In another embodiment, tibial component 100 includes only a single cavity (not shown). First cavity 124 and second cavity 126 may include a xy plane cross-section having any of various shapes, including for example, square, quadrilateral, elliptical, circular semi-circular, and any regular or irregular polygonal shapes. First cavity 124 and second cavity 126 may include an xz plane cross-section having any of various shapes, including for example, square, quadrilateral, elliptical, circular semi-circular, and any regular or irregular polygonal shapes. First cavity 124 and second cavity 126 may include a yz plane cross-section having any of various shapes, including for example, square, quadrilateral, elliptical, circular semi-circular, and any regular or irregular polygonal shapes. In one embodiment, tibial component 100 comprises first cavity 124 and second cavity 126 positioned substantially opposite first condyle contact surface 110 and second cavity contact surface 114, respectively.

First bearing portion 120 may comprise a first bearing portion length (not shown), a first bearing portion width 130, and a first bearing portion thickness 132. In one embodiment, varying at least one of first bearing portion length (not shown), first bearing portion width 130, and a first bearing portion thickness 132 causes the tensile stress within first bearing portion 120 to change. Additionally, second bearing portion 122 may comprise a second bearing portion length (not shown), a second bearing portion width 134, and a second bearing portion thickness 136. In one embodiment, varying at least one of second bearing portion length (not shown), second bearing portion width 134, and a second bearing portion thickness 136 causes the tensile stress within second bearing portion 122 to change. In one embodiment, first bearing portion thickness 132 is substantially uniform across first bearing portion width 130. In another embodiment, second bearing portion thickness 136 is substantially uniform across second bearing portion width 134.

For example, decreasing first bearing portion thickness 132 may increase the tensile stress within first bearing portion 120. In another example, decreasing first bearing portion length (not shown) and first bearing portion width 130 may decrease the tensile stress within first bearing portion 120. Any combination of varying first bearing portion length (not shown), first bearing portion width 130, first bearing portion thickness 132, second bearing portion length (not shown), second bearing portion width 134, and second bearing portion thickness 136 is contemplated to increase or decrease the tensile stress within first bearing portion 120 and second bearing portion 122. Such increase or decrease in the tensile stress within first bearing portion 120 and second bearing portion 122 may result in an increase or decrease in the cushioning effect in tibial component 100.

In one embodiment, first bearing portion thickness 132 and second bearing portion thickness 136 is between about 2 mm and about 12 mm. In another embodiment, first bearing portion thickness 132 and second bearing portion thickness 136 is between about 4 mm and about 8 mm. In another embodiment, first bearing portion thickness 132 and second bearing portion thickness 136 is greater than about 6 mm.

First cavity 124 may comprise a first cavity length (not shown), a first cavity width 138, and a first cavity height 140. In one embodiment, varying at least one of first cavity length (not shown), a first cavity width 138, and a first cavity height 140 causes the tensile stress within first bearing portion 120 to change. Additionally, second cavity 126 may comprise a second cavity length (not shown), a second cavity width 142, and a second cavity height 144. In one embodiment, varying at least one of second cavity 126 may comprise a second cavity length (not shown), a second cavity width 142, and a second cavity height 144 causes the tensile stress within second bearing portion 122 to change.

For example, decreasing first cavity height 140 may decrease the tensile stress within first bearing portion 120. In another example, decreasing first cavity length (not shown) and first cavity width 138 may decrease the tensile stress within first bearing portion 120. Any combination of varying first cavity length (not shown), first cavity width 138, first cavity height 140, second cavity length (not shown), second cavity width 142, and second cavity height 144 is contemplated to increase or decrease the tensile stress within first bearing portion 120 and second bearing portion 122. Such increase or decrease in the tensile stress within first bearing portion 120 and second bearing portion 122 may result in an increase or decrease in the cushioning effect in tibial component 100.

Tibial component 100 may additionally comprise a body portion thickness 146 defined as the distance between upper surface 106 and lower surface 116. In one embodiment, body portion thickness 146 is between about 4 mm and about 30 mm. In another embodiment, body portion thickness 146 is between about 8 mm and about 20 mm. In another embodiment, body portion thickness 146 is between about 10 mm and about 18 mm. In another embodiment, body portion thickness 146 is between about 12 mm and about 16 mm.

In one embodiment, the cushioning characteristic of tibial component 100 further leads to conformance of at least one of first condyle contact surface 110 and second condyle contact surface 114 with the at least one condyle (not shown) of the femoral component (not shown). The cushioning and conformance effects of tibial component 100 may lead to reduced and dampened axial loads and increased surface contact area of the interface between at least one of first condyle contact surface 110 and second condyle contact surface 114 with the at least one condyle (not shown) of the femoral component (not shown). In one embodiment, an increased surface contact area of the interface between at least one of first condyle contact surface 110 and second condyle contact surface 114 with the at least one condyle (not shown) of the femoral component (not shown) reduces high stress areas in at least one of first condyle contact surface 110 and second condyle contact surface 114 by spreading the load from the femoral component (not shown) more evenly. In another embodiment, reduced stress in at least one of first condyle contact surface 110 and second condyle contact surface 114 provides increased wear characteristics in tibial component 100.

Figure 2:
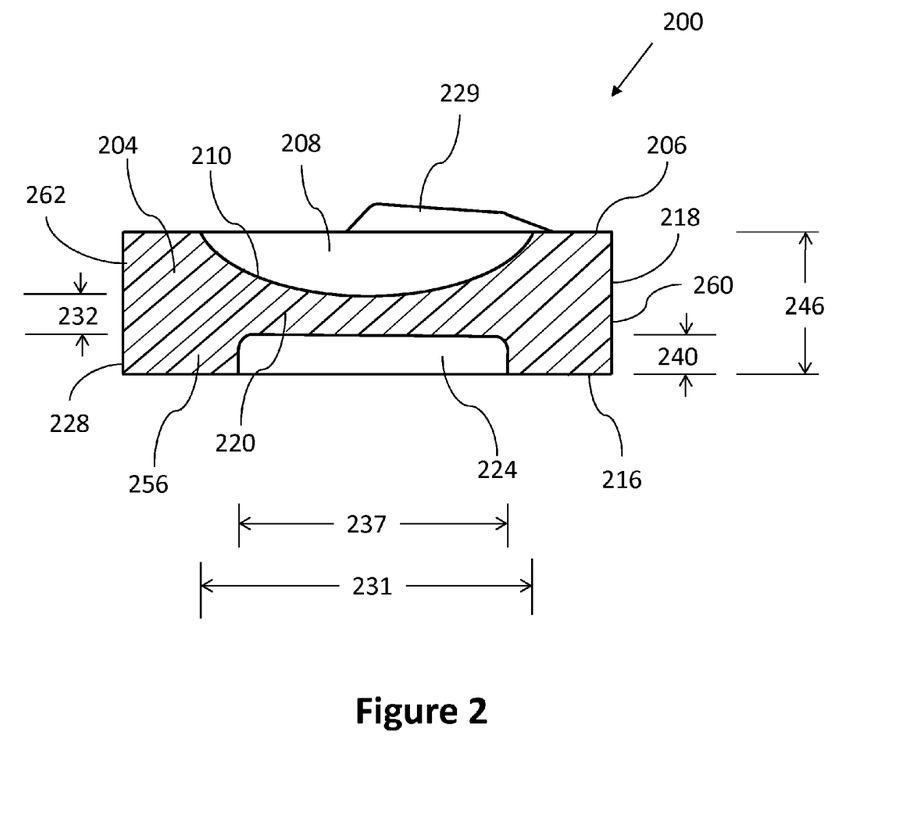
FIG. 2 illustrates an example arrangement of a tibial component of a knee joint prosthesis.

FIG. 2 illustrates a view in detail of the portion indicated by the section lines 2-2 in FIG. 1. FIG. 2 illustrates an example arrangement of a tibial component 200 of a total knee joint prosthesis, including a body portion 204 and an upper surface 206. Tibial component 200 further comprises a first concave fossae 208 including a first condyle contact surface 210. Tibial component 200 additionally includes a lower surface 216 and a side portion 218 extending between upper surface 206 and lower surface 216. Tibial component 200 comprises a first bearing portion 220. Tibial component 200 includes at least one cavity extending into body portion 204 from lower surface 216, such as first cavity 224. FIG. 2 illustrates an embodiment of tibial component 200 wherein first cavity 224 comprises a yz plane cross-section having a substantially rectangular quadrilateral shape. Tibial component 200 may additionally include a rim portion 228 capable of operatively connecting tibial component 200 to a substantially rigid tibial tray (not shown). Tibial component 200 may further include a center post 229 extending from body portion 204.

As illustrated in FIG. 2, tibial component 200 may include a first bearing portion length 231 and first bearing portion thickness 232. Additionally, tibial component 200 may include a first cavity length 237 and first cavity height 240. Finally, tibial component 200 may include a body portion thickness 246. Tibial component 200 may additionally include a first lateral side portion 256, a posterior side portion 260, and an anterior side portion 262. In one embodiment, upper surface 206 is angled such that anterior side portion 262 comprises a greater thickness than posterior side portion 260.

Figure 3:
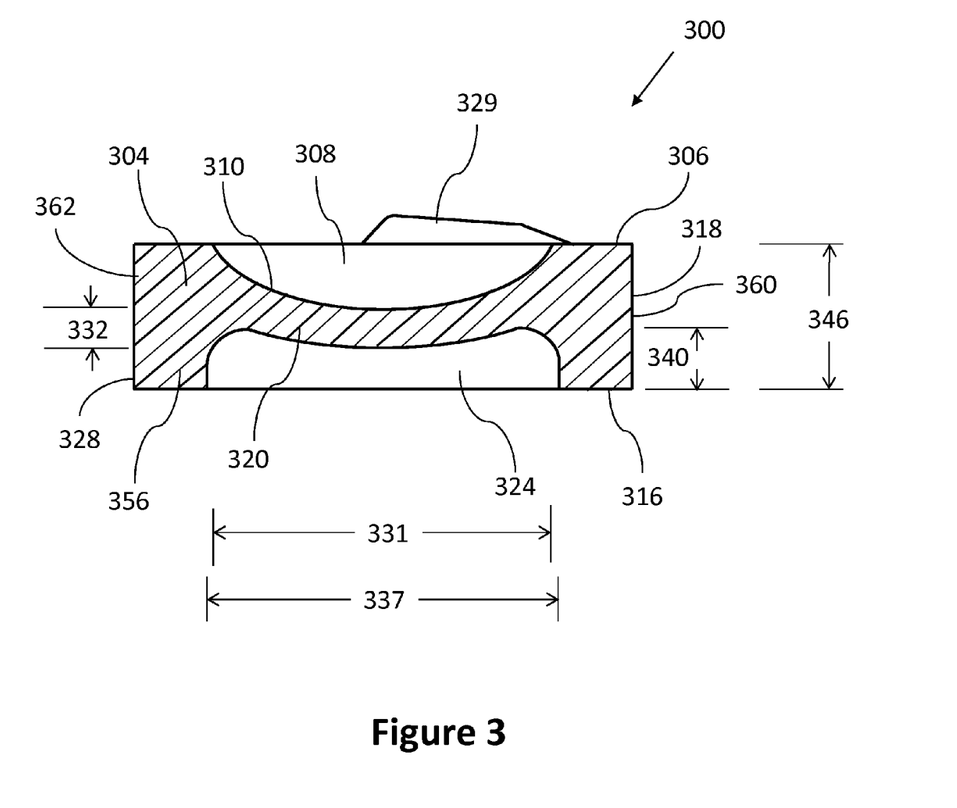
FIG. 3 illustrates an example arrangement of a tibial component of a knee joint prosthesis.

FIG. 3 illustrates an alternative view in detail of the portion indicated by the section lines 2-2 in FIG. 1. FIG. 3 illustrates an example arrangement of a tibial component 300 of a total knee joint prosthesis, including a body portion 304 and an upper surface 306. Tibial component 300 further comprises a first concave fossae 308 including a first condyle contact surface 310. Tibial component 300 additionally includes a lower surface 316 and a side portion 318 extending between upper surface 306 and lower surface 316. Tibial component 300 comprises a first bearing portion 320. Tibial component 300 includes at least one cavity extending into body portion 304 from lower surface 316, such as first cavity 324. FIG. 3 illustrates an embodiment of tibial component 300 wherein first cavity 324 comprises a yz plane cross-section having an arcuate upper surface. Tibial component 300 may additionally include a rim portion 328 capable of operatively connecting tibial component 300 to a substantially rigid tibial tray (not shown). Tibial component 300 may further include a center post 329 extending from body portion 304.

As illustrated in FIG. 3, tibial component 300 may include a first bearing portion length 331 and first bearing portion thickness 332. As illustrated in FIG. 3, tibial component 300 may include a first bearing portion 320 comprising a first bearing portion thickness 332 that is substantially uniform. In one embodiment, tibial component 300 may include a second bearing portion (not shown) comprising a second bearing portion thickness (not shown) that is substantially uniform. Additionally, tibial component 300 may include a first cavity length 337 and first cavity height 340. Finally, tibial component 300 may include a body portion thickness 346. Tibial component 300 may additionally include a first lateral side portion 356, an anterior side portion 360, and a posterior side portion 362.

Figure 4:
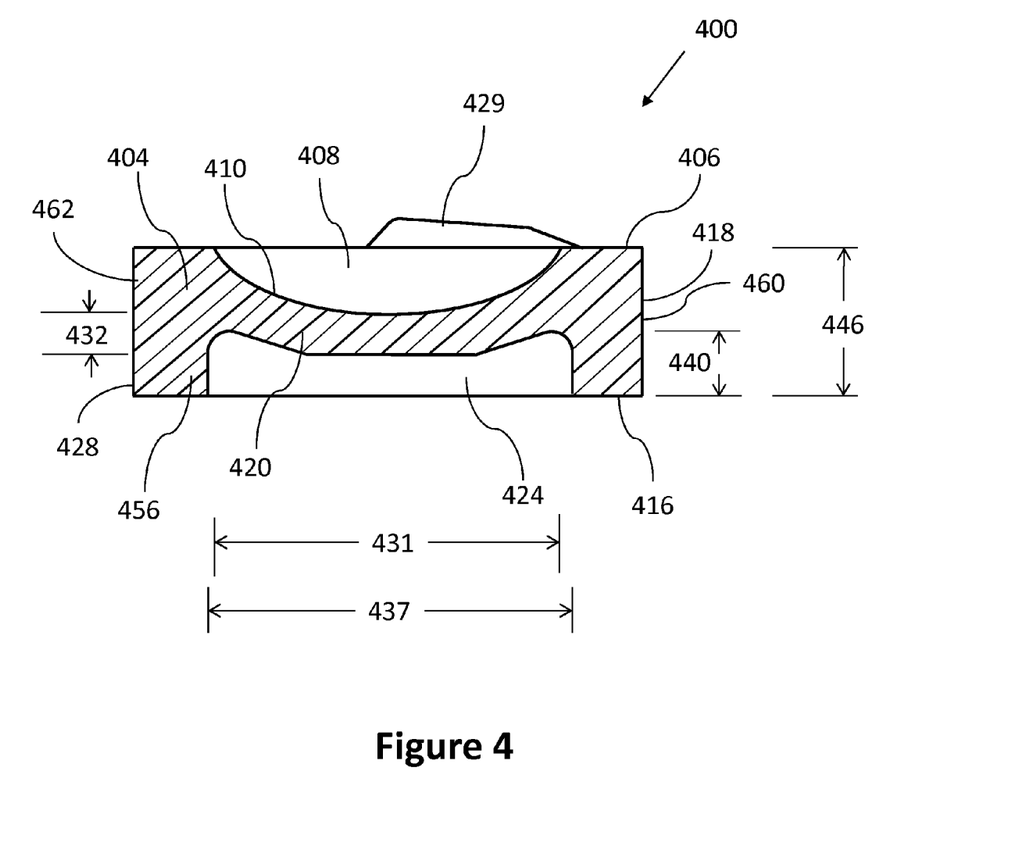
FIG. 4 illustrates an example arrangement of a tibial component of a knee joint prosthesis.

FIG. 4 illustrates an alternative view in detail of the portion indicated by the section lines 2-2 in FIG. 1. FIG. 4 illustrates an example arrangement of a tibial component 400 of a total knee joint prosthesis, including a body portion 404 and an upper surface 406. Tibial component 400 further comprises a first concave fossae 408 including a first condyle contact surface 410. Tibial component 400 additionally includes a lower surface 416 and a side portion 418 extending between upper surface 406 and lower surface 416. Tibial component 400 comprises a first bearing portion 420. Tibial component 400 includes at least one cavity extending into body portion 404 from lower surface 416, such as first cavity 424. FIG. 4 illustrates an embodiment of tibial component 400 wherein first cavity 424 comprises a yz plane cross-section having an upper surface comprising a plurality of planar components extending transversely along tibial component 400 and angled with respect to one another. Tibial component 400 may additionally include a rim portion 428 capable of operatively connecting tibial component 400 to a substantially rigid tibial tray (not shown). Tibial component 400 may further include a center post 429 extending from body portion 404.

As illustrated in FIG. 4, tibial component 400 may include a first bearing portion length 431 and first bearing portion thickness 432. Additionally, tibial component 400 may include a first cavity length 437 and first cavity height 440. Finally, tibial component 400 may include a body portion thickness 446. Tibial component 400 may additionally include a first lateral side portion 456, a posterior side portion 460, and an anterior side portion 462. In one embodiment, upper surface 406 is angled such that anterior side portion 462 comprises a greater thickness than posterior side portion 460.

Figure 5:
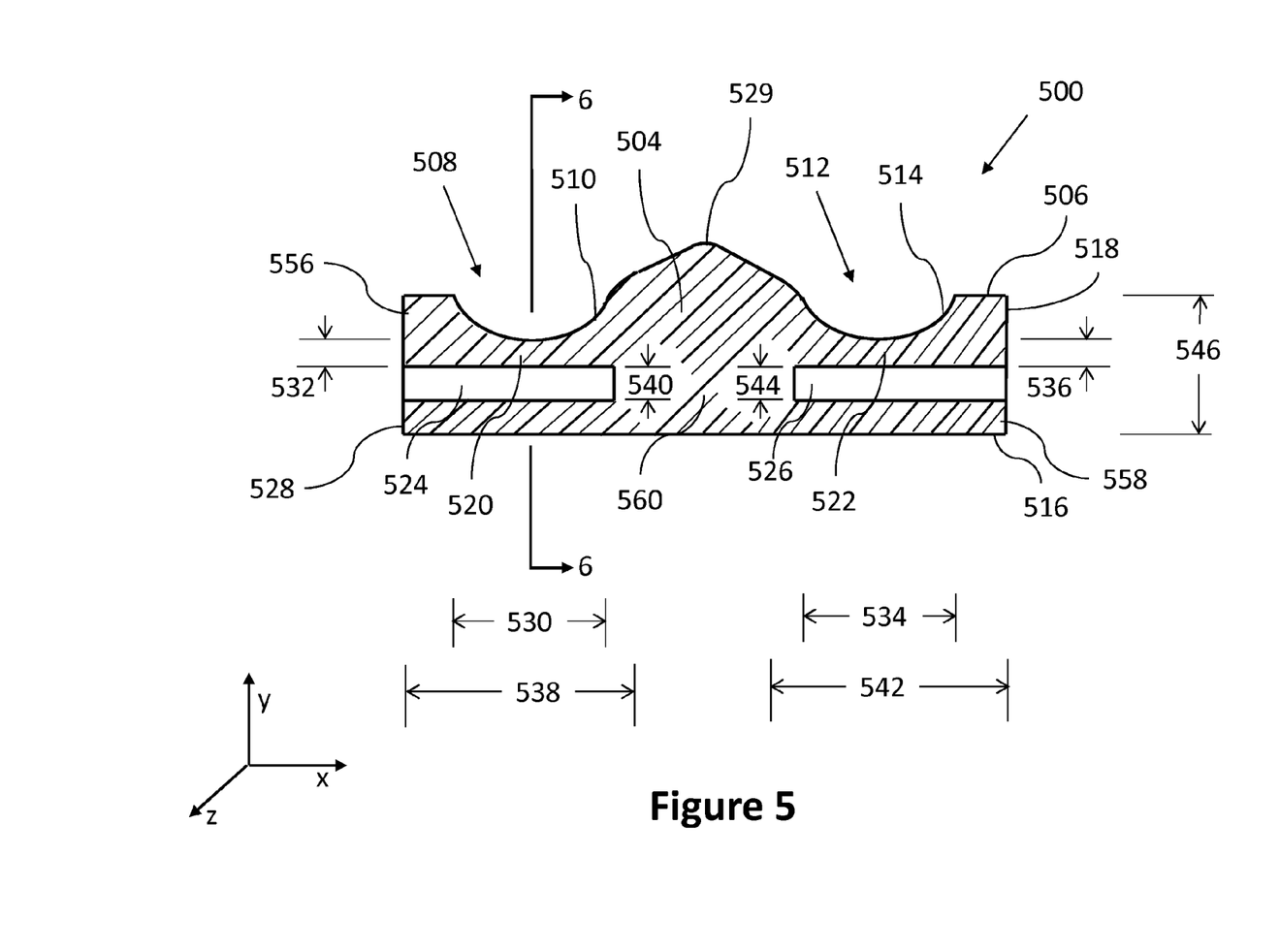
FIG. 5 illustrates an example arrangement of a tibial component of a knee joint prosthesis.

FIG. 5 illustrates a front view of an example arrangement of a tibial component 500 of a total knee joint prosthesis, including a body portion 504 and an upper surface 506. Tibial component 500 further comprises a first concave fossae 508 including a first condyle contact surface 510, as well as a second concave fossae 512 including a second condyle contact surface 514. Tibial component 500 additionally includes a lower surface 516 and a side portion 518 extending between upper surface 506 and lower surface 516. Tibial component 500 comprises a first bearing portion 520 and a second bearing portion 522. Tibial component 500 includes at least one cavity extending into body portion 504 from side portion 518, such as first cavity 524 and second cavity 526. Tibial component 500 may additionally include a rim portion 528 capable of operatively connecting tibial component 500 to a substantially rigid tibial tray (not shown). Tibial component 500 may further include a center post 529 extending from body portion 504. First bearing portion 520 may comprise a first bearing portion length (not shown), a first bearing portion width 530, and a first bearing portion thickness 532. Second bearing portion 522 may comprise a second bearing portion length (not shown), a second bearing portion width 534, and a second bearing portion thickness 536. First cavity 524 may comprise a first cavity length (not shown), a first cavity width 538, and a first cavity height 540. Second cavity 526 may comprise a second cavity length (not shown), a second cavity width 542, and a second cavity height 544. Tibial component 500 may additionally comprise a body portion thickness 546 defined as the distance between upper surface 506 and lower surface 516.

Tibial component 500 may additionally include a first lateral side portion 556, a second lateral side portion 558, and a posterior side portion 560. In one embodiment, at least one cavity extends into body portion 504 from one or more of first lateral side portion 556, second lateral side portion 558, an anterior side portion (not shown), and posterior side portion 560.

In one embodiment, tibial component 500 includes a plurality of cavities, for example, first cavity 524 and second cavity 526 illustrated in FIG. 5. In another embodiment, tibial component 500 includes only a single cavity (not shown). First cavity 524 and second cavity 526 may include a xy plane cross-section having any of various shapes, including for example, square, quadrilateral, elliptical, circular semi-circular, and any regular or irregular polygonal shapes. First cavity 524 and second cavity 526 may include an xz plane cross-section having any of various shapes, including for example, square, quadrilateral, elliptical, circular semi-circular, and any regular or irregular polygonal shapes. First cavity 524 and second cavity 526 may include a yz plane cross-section having any of various shapes, including for example, square, quadrilateral, elliptical, circular semi-circular, arcuate, and any regular or irregular polygonal shapes. In one embodiment, tibial component 500 comprises first cavity 524 and second cavity 526 positioned substantially opposite first condyle contact surface 510 and second cavity contact surface 514, respectively.

Figure 6:
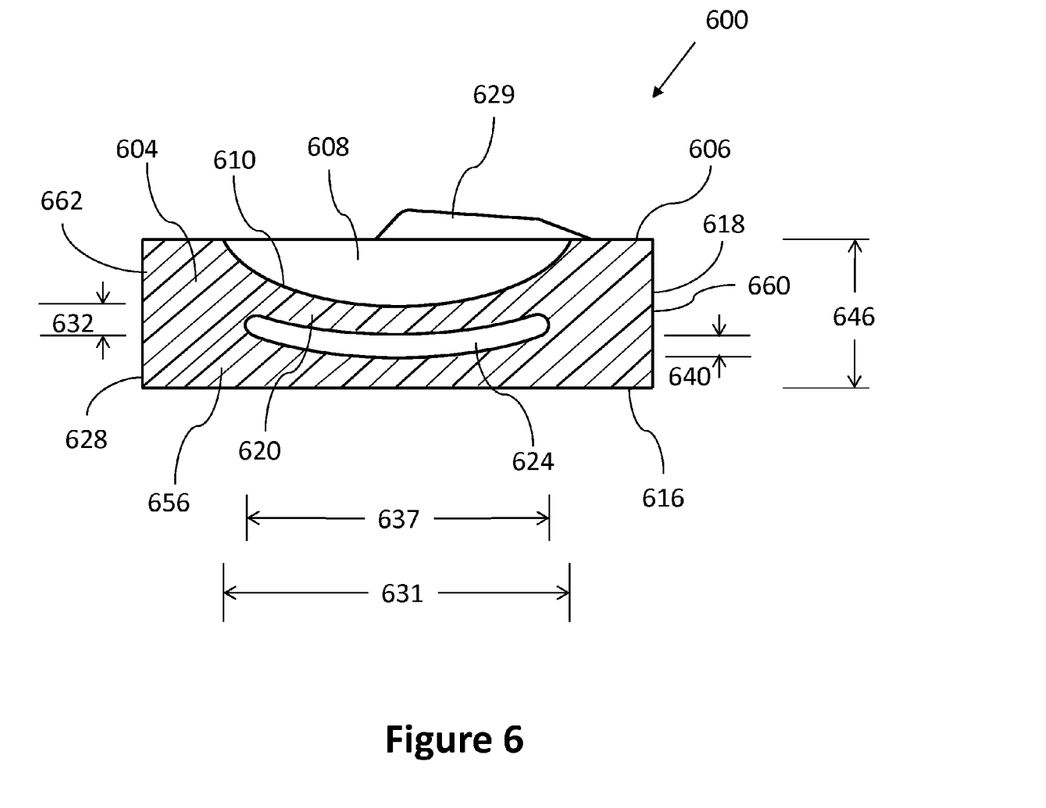
FIG. 6 illustrates an example arrangement of a tibial component of a knee joint prosthesis.

FIG. 6 illustrates a view in detail of the portion indicated by the section lines 6-6 in FIG. 5. FIG. 6 illustrates an example arrangement of a tibial component 600 of a total knee joint prosthesis, including a body portion 604 and an upper surface 606. Tibial component 600 further comprises a first concave fossae 608 including a first condyle contact surface 610. Tibial component 600 additionally includes a lower surface 616 and a side portion 618 extending between upper surface 606 and lower surface 616. Tibial component 600 comprises a first bearing portion 620. Tibial component 600 includes at least one cavity extending into body portion 604 from side portion 618, such as first cavity 624. FIG. 6 illustrates an embodiment of tibial component 600 wherein first cavity 624 comprises a yz plane cross-section having a substantially arcuate shape. Tibial component 600 may additionally include a rim portion 628 capable of operatively connecting tibial component 600 to a substantially rigid tibial tray (not shown). Tibial component 600 may further include a center post 629 extending from body portion 604.

As illustrated in FIG. 6, tibial component 600 may include a first bearing portion length 631 and first bearing portion thickness 632. Additionally, tibial component 600 may include a first cavity length 637 and first cavity height 640. Finally, tibial component 600 may include a body portion thickness 646.

Tibial component 600 may additionally include a first lateral side portion 656, a posterior side portion 660, and an anterior side portion 662. In one embodiment, at least one cavity extends into body portion 604 from one or more of first lateral side portion 656, anterior side portion 662, posterior side portion 660, and a second lateral side portion (not shown). In one embodiment, upper surface 606 is angled such that anterior side portion 662 comprises a greater thickness than posterior side portion 660.

Figure 7:
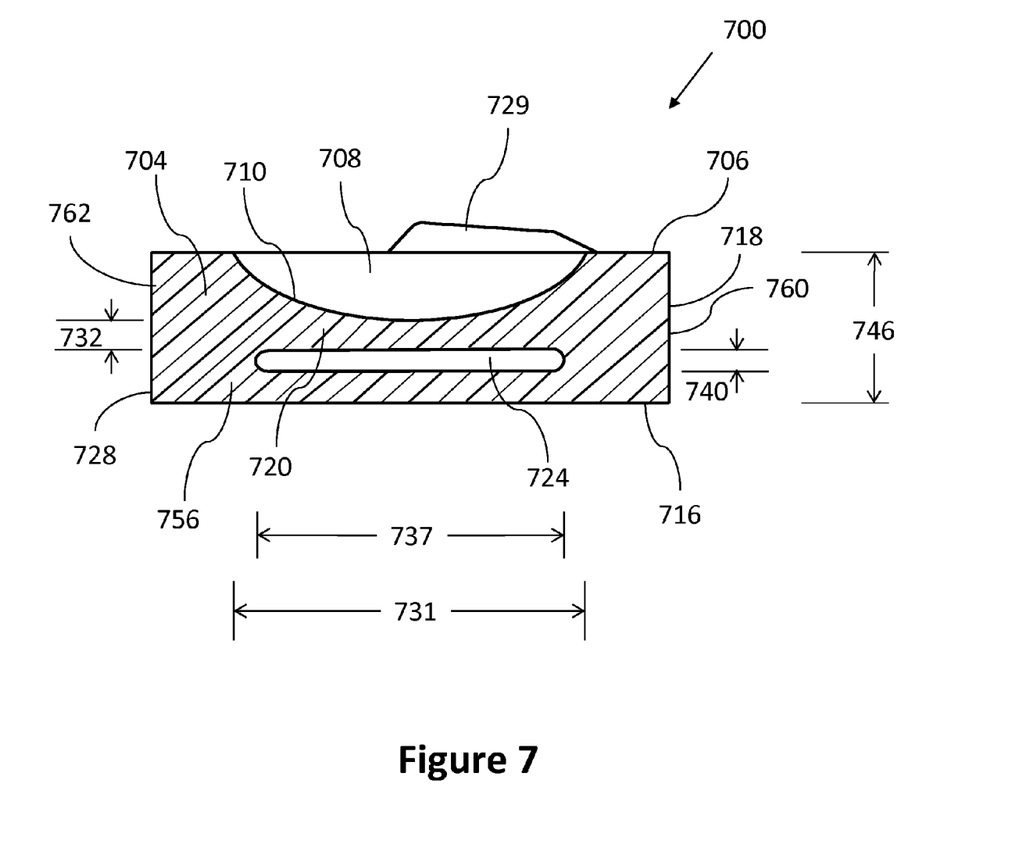
FIG. 7 illustrates an example arrangement of a tibial component of a knee joint prosthesis.

FIG. 7 illustrates an alternative view in detail of the portion indicated by the section lines 6-6 in FIG. 5. FIG. 7 illustrates an example arrangement of a tibial component 700 of a total knee joint prosthesis, including a body portion 704 and an upper surface 706. Tibial component 700 further comprises a first concave fossae 708 including a first condyle contact surface 710. Tibial component 700 additionally includes a lower surface 716 and a side portion 718 extending between upper surface 706 and lower surface 716. Tibial component 700 comprises a first bearing portion 720. Tibial component 700 includes at least one cavity extending into body portion 704 from side portion 718, such as first cavity 724. FIG. 7 illustrates an embodiment of tibial component 700 wherein first cavity 724 comprises a yz plane cross-section having a rounded-end rectangular shape. Tibial component 700 may additionally include a rim portion 728 capable of operatively connecting tibial component 700 to a substantially rigid tibial tray (not shown). Tibial component 700 may further include a center post 729 extending from body portion 704.

As illustrated in FIG. 7, tibial component 700 may include a first bearing portion length 731 and first bearing portion thickness 732. Additionally, tibial component 700 may include a first cavity length 737 and first cavity height 740. Finally, tibial component 700 may include a body portion thickness 746.

Tibial component 700 may additionally include a first lateral side portion 756, a posterior side portion 760, and an anterior side portion 762. In one embodiment, at least one cavity extends into body portion 704 from one or more of first lateral side portion 756, anterior side portion 762, posterior side portion 760, and a second lateral side portion (not shown). In one embodiment, upper surface 706 is angled such that anterior side portion 762 comprises a greater thickness than posterior side portion 760.

Figure 8:
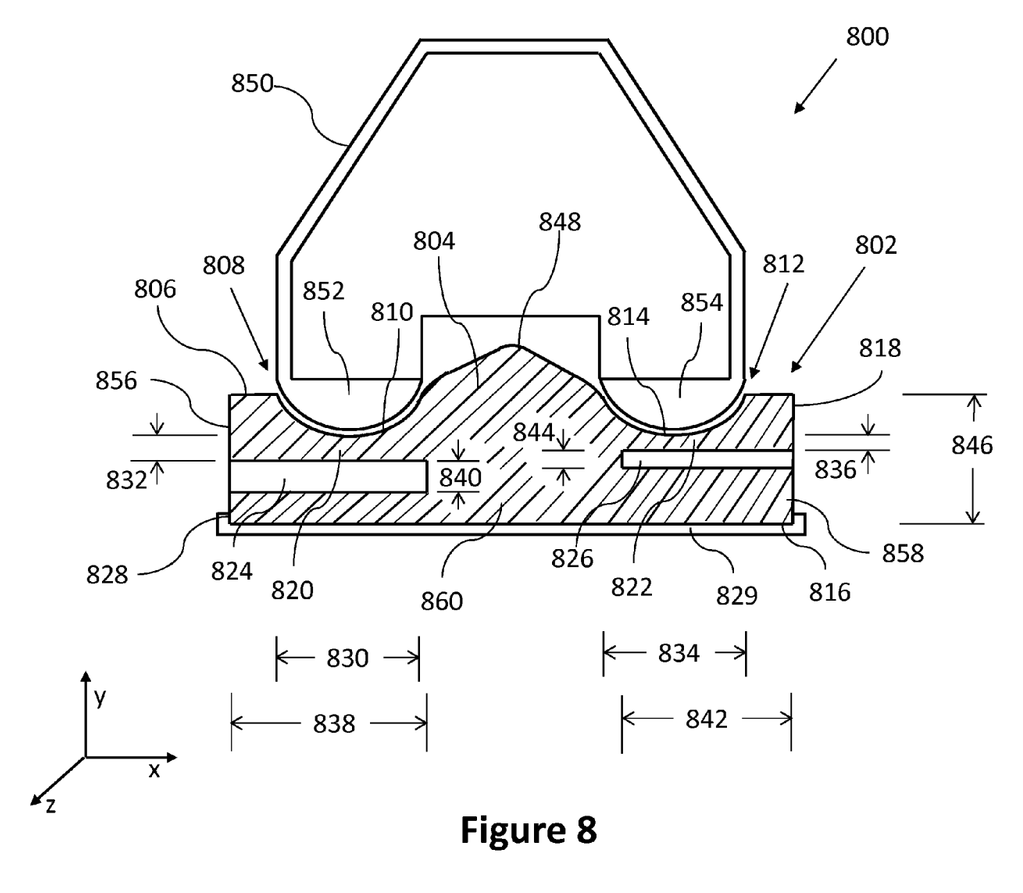
FIG. 8 illustrates an example arrangement of a total knee joint prosthesis.

FIG. 8 illustrates a front view of an example arrangement of a total knee joint prosthesis 800, including a tibial component 802. Tibial component 802 includes a body portion 804 and an upper surface 806. Tibial component 802 further comprises a first concave fossae 808 including a first condyle contact surface 810, as well as a second concave fossae 812 including a second condyle contact surface 814. Tibial component 802 additionally includes a lower surface 816 and a side portion 818 extending between upper surface 806 and lower surface 816. Tibial component 802 comprises a first bearing portion 820 and a second bearing portion 822. Tibial component 802 includes at least one cavity. As illustrated in FIG. 8, the at least one cavity extends into body portion 804 from side portion 818, such as first cavity 824 and second cavity 826. Tibial component 802 may additionally include a rim portion 828 capable of operatively connecting tibial component 802 to a substantially rigid tibial tray 829.

First bearing portion 820 may comprise a first bearing portion length (not shown), a first bearing portion width 830, and a first bearing portion thickness 832. Second bearing portion 822 may comprise a second bearing portion length (not shown), a second bearing portion width 834, and a second bearing portion thickness 836. First cavity 824 may comprise a first cavity length (not shown), a first cavity width 838, and a first cavity height 840. Second cavity 826 may comprise a second cavity length (not shown), a second cavity width 842, and a second cavity height 844. As illustrated in FIG. 8, first bearing portion thickness 832 may be greater than second bearing portion thickness 836. Likewise, first cavity height 840 may be greater than second cavity height 844. Additionally, first cavity width 838 may be greater than second cavity width 842. It is contemplated that any combination of first bearing portion length (not shown), first bearing portion width 830, first bearing portion thickness 832, second bearing portion length (not shown), second bearing portion width 834, second bearing portion thickness 836, first cavity length (not shown), first cavity width 838, first cavity height 840, second cavity length (not shown), second cavity width 842, and second cavity height 844 can be utilized to vary the tensile stress in first bearing portion 820 and second bearing portion 822, which in turn may alter the cushioning effect of tibial component 802.

Tibial component 802 may additionally comprise a body portion thickness 846 defined as the distance between upper surface 806 and lower surface 816. Tibial component 802 may further include a center post 848 extending from body portion 804.

Total knee joint prosthesis 800 may include a femoral component 850 comprising a first condyle 852 and a second condyle 854. In one embodiment, femoral component 850 includes at least one condyle. Femoral component 850 may be formed of any of a number of materials, including for example, a metal, a polymer, an alloy, and a composite. In one embodiment, femoral component 850 comprises a substantially rigid material. In another embodiment, femoral component 850 is formed of a metal. In one embodiment, femoral component 850 is operatively connected to an individual's femur. In another embodiment, femoral component 850 is configured to fit over a resected femur via a surgical implant.

First condyle 852 may be configured to operatively connect to tibial component 802 via first condyle contact surface 810. Second condyle 854 may be configured to operatively connected to tibial component 802 via second condyle contact surface 814. First condyle 852 and second condyle 854 may be formed in a variety of shapes, including a shape substantially the same as that of first concave fossae 808 and second concave fossae 812, so as to facilitate engagement of first condyle 852 and second condyle 854 with first concave fossae 808 and second concave fossae 812, respectively. First condyle 852 and second condyle 854 may include an xz plane cross-section having any of various shapes, including oval, elliptical, and quadrilateral. First condyle 852 and second condyle 854 may include a xy plane cross-section having any of various shapes, including semi-circular, semi-elliptical, and quadrilateral. First condyle 852 and second condyle 854 may include a yz plane cross-section having any of various shapes, including semi-circular and semi-elliptical.

First condyle 852 and first condyle contact surface 810, and second condyle 854 and second condyle contact surface 814 may include varying degrees of conformity with one another. In one embodiment, one or more radii of curvature of first condyle 852 and/or second condyle 854 may be less than one or more radii of curvature of first condyle contact surface 810 and second condyle contact surface 814, respectively. In another embodiment, one or more radii of curvature of first condyle 852 and/or second condyle 854 may be equal to one or more radii of curvature of first condyle contact surface 810 and second condyle contact surface 814, respectively. In another embodiment, one or more radii of curvature of first condyle 852 and/or second condyle 854 may be greater than one or more radii of curvature of first condyle contact surface 810 and second condyle contact surface 814, respectively. In another embodiment, one or more radii of curvature of first condyle contact surface 810 and second condyle contact surface 814 may increase or decrease as a result of the load placed upon first condyle contact surface 810 and second condyle contact surface 814. In another embodiment, first condyle contact surface 810 and second condyle contact surface 814 may have radii of curvature that conform to the radii of curvature of first condyle 852 and second condyle 854, respectively, upon application of a load upon tibial component 802 by femoral component 850.

In one embodiment, tibial component 802 may additionally include a first lateral side portion 856, a second lateral side portion 858, and a posterior side portion 860. In one embodiment, at least one cavity extends into body portion 804 from one or more of first lateral side portion 856, second lateral side portion 858, an anterior side portion (not shown), and posterior side portion 860.

Tibial tray 829 may be formed of any of a number of materials, including for example, a metal, a polymer, an alloy, and a composite. In one embodiment, tibial tray 829 comprises a substantially rigid material. In another embodiment, tibial tray 829 is formed of a metal. In one embodiment, tibial tray 829 is operatively connected to an individual's tibia. In another embodiment, tibial tray 829 is configured to fit over a resected tibia via a surgical implant. In one embodiment, tibial component 802 is capable of being connected to a tibial tray 829 via rim portion 828. Rim portion 828 may comprise a recessed groove or prominent ridge configured to engage a corresponding ridge or groove within a tibial tray 829. In another embodiment, tibial component 802 is configured to attach to tibial tray 829 through any attachment means, including for example, fasteners, a screw interface, friction fit, and adhesives.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. As used in the specification and the claims, the singular forms "a," "an," and "the" include the plural. Finally, where the term "about" is used in conjunction with a number, it is intended to include ±10% of the number. In other words, "about 10" may mean from 9 to 11.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

What is claimed is:

1. A tibial component of a knee joint prosthesis, the tibial component comprising:
   a body portion;
   an upper surface;
   a first concave fossae comprising a first condyle contact surface;
   a second concave fossae comprising a second condyle contact surface;
   a lower outer surface;
   a side portion extending between the upper surface and the lower outer surface;
   a first bearing portion;
   a second bearing portion; and
   a first cavity extending into the body portion from the lower outer surface and a second cavity extending into the body portion from the lower outer surface,
      wherein the first cavity is positioned substantially opposite the first condyle contact surface and the second cavity is positioned substantially opposite the second condyle contact surface;
   wherein a load applied substantially normally to the first condyle contact surface and the second condyle contact surface causes a tensile stress within the first bearing portion and the second bearing portion, and a compressive stress within the side portion.

2. The tibial component of claim 1, wherein the tibial component is comprised of a substantially rigid material.

3. The tibial component of claim 1, wherein the tibial component is comprised of a polymeric material having a Shore hardness greater than 65.

4. The tibial component of claim 1, wherein at least one of the first condyle contact surface, the second condyle contact surface, and the upper surface is capable of operatively connecting the tibial component to a substantially rigid femoral component comprising a first condyle and a second condyle.

5. The tibial component of claim 1, wherein:
   the first bearing portion comprises a first bearing portion length, a first bearing portion width, and a first bearing portion thickness;
   the second bearing portion comprises a second bearing portion length, a second bearing portion width, and a second bearing portion thickness;
   wherein varying at least one of the first bearing portion length, the first bearing portion width, and the first bearing portion thickness causes the tensile stress within the first bearing portion to change; and
   wherein varying at least one of the second bearing portion length, the second bearing portion width, and the second bearing portion thickness causes the tensile stress within the second bearing portion to change.

6. The tibial component of claim 1, wherein:
   the first cavity comprises a first cavity length, a first cavity width, and a first cavity height;
   the second cavity comprises a second cavity length, a second cavity width, and a second cavity height;
   wherein varying at least one of the first cavity length, the first cavity width, and the first cavity height causes the tensile stress within the first bearing portion to change; and
   wherein varying at least one of the second cavity length, the second cavity width, and the second cavity height causes the tensile stress within the second bearing portion to change.

7. The tibial component of claim 1, wherein a distance between the upper surface and the lower outer surface is between about 8 mm and about 30 mm.

8. The tibial component of claim 1, wherein:
   the first bearing portion comprises a first bearing portion thickness and a first bearing portion width;
   the second bearing portion comprises a second bearing portion thickness and a second bearing portion width;
   wherein the first bearing portion thickness is uniform across the first bearing portion width; and
   wherein the second bearing portion thickness is uniform across the second bearing portion width.

9. A total knee joint prosthesis, the total knee joint prosthesis comprising:
   a substantially rigid femoral component comprising a first condyle and a second condyle; and a substantially rigid tibial component, comprising:
  a body portion;
  an upper surface;
  a first concave fossae comprising a first condyle contact surface; and
  a second concave fossae comprising a second condyle contact surface;
  a lower outer surface;
  a side portion extending between the upper surface and the lower outer surface
  a first bearing portion;
  a second bearing portion; and
  a first cavity;
  a second cavity;
  wherein the first cavity and the second cavity extend into the body portion from the lower outer surface,
  wherein the first cavity is positioned substantially opposite the first condyle contact surface and the second cavity is positioned substantially opposite the second condyle contact surface;
  wherein the first condyle operatively connects to the first condyle contact surface and the second condyle operatively connects to the second condyle contact surface; and
  wherein a load applied by the first condyle and the second condyle substantially normally to the first condyle contact surface and the second condyle contact surface causes a tensile stress within the first bearing portion and the second bearing portion, and a compressive stress within the side portion.

10. The total knee joint prosthesis of claim 9, wherein the tibial component is comprised of a polymeric material having a Shore hardness greater than 65.

11. The total knee joint prosthesis of claim 9, wherein:
  the first bearing portion comprises a first bearing portion length, a first bearing portion width, and a first bearing portion thickness;
  the second bearing portion comprises a second bearing portion length, a second bearing portion width, and a second bearing portion thickness;
  wherein varying at least one of the first bearing portion length, the first bearing portion width, and the first bearing portion thickness causes the tensile stress within the first bearing portion to change; and
  wherein varying at least one of the second bearing portion length, the second bearing portion width, and the second bearing portion thickness causes the tensile stress within the second bearing portion to change.

12. The total knee joint prosthesis of claim 9, wherein:
  the first cavity comprises a first cavity length, a first cavity width, and a first cavity height;
  the second cavity comprises a second cavity length, a second cavity width, and a second cavity height;
  wherein varying at least one of the first cavity length, the first cavity width, and the first cavity height causes the tensile stress within the first bearing portion to change; and
  wherein varying at least one of the second cavity length, the second cavity width, and the second cavity height causes the tensile stress within the second bearing portion to change.

13. The total knee joint prosthesis of claim 9, wherein the substantially rigid tibial component is comprised of a substantially rigid material.

14. The total knee joint prosthesis of claim 9, wherein a distance between the upper surface and the lower outer surface is between about 8 mm and about 30 mm.

15. The total knee joint prosthesis of claim 9, wherein:
  the first bearing portion comprises a first bearing portion thickness and a first bearing portion width;
  the second bearing portion comprises a second bearing portion thickness and a second bearing portion width;
  wherein the first bearing portion thickness is uniform across the first bearing portion width; and
  wherein the second bearing portion thickness is uniform across the second bearing portion width.

* * * * *